United States Patent
Kim et al.

(10) Patent No.: US 12,409,229 B2
(45) Date of Patent: Sep. 9, 2025

(54) SYNTHESIZING DRUG-ORGANIC-ACID-ANHYDRIDE CONJUGATES WITHOUT USING COUPLING REAGENT

(71) Applicant: CNPharm Co., Ltd., Seoul (KR)

(72) Inventors: Hojun Kim, Seoul (KR); Kwang Sik Park, Seoul (KR); Guen-Woo Jin, Seoul (KR)

(73) Assignee: CNPharm Co., Ltd., Seoul (KR)

( * ) Notice: Subject to any disclaimer, the term of this patent is extended or adjusted under 35 U.S.C. 154(b) by 107 days.

(21) Appl. No.: 17/228,203

(22) Filed: Apr. 12, 2021

(65) Prior Publication Data

US 2021/0315998 A1    Oct. 14, 2021

Related U.S. Application Data

(60) Provisional application No. 63/048,454, filed on Jul. 6, 2020, provisional application No. 63/045,518, filed on Jun. 29, 2020, provisional application No. 63/043,579, filed on Jun. 24, 2020, provisional application No. 63/038,444, filed on Jun. 12, 2020, provisional application No. 63/037,477, filed on Jun. 10, 2020, provisional application No. 63/037,474, filed on Jun. 10, 2020, provisional application No. 63/030,594, filed on May 27, 2020, provisional application No. 63/030,103, filed on May 26, 2020, provisional application No. 63/009,312, filed on Apr. 13, 2020.

(51) Int. Cl.
| | | |
|---|---|---|
| A61K 47/60 | (2017.01) | |
| A61K 47/54 | (2017.01) | |
| C07D 323/02 | (2006.01) | |
| C07D 325/00 | (2006.01) | |

(52) U.S. Cl.
CPC ............ *A61K 47/545* (2017.08); *A61K 47/60* (2017.08); *C07D 323/02* (2013.01); *C07D 325/00* (2013.01)

(58) Field of Classification Search
CPC .................................................. A61K 47/545
See application file for complete search history.

(56) References Cited

FOREIGN PATENT DOCUMENTS

WO    WO2015137777    *    9/2015

\* cited by examiner

*Primary Examiner* — Nizal S Chandrakumar
(74) *Attorney, Agent, or Firm* — Procopio, Cory, Hargreaves & Savitch LLP

(57) ABSTRACT

Synthesizing a drug-organic-acid-anhydride conjugate using docetaxel as a drug, including: mixing aconitic anhydride with a chlorinating reagent to produce a first mixture; dissolving the first mixture in an organic solvent to produce a dissolved mixture; stirring the dissolved mixture; evaporating the organic solvent from the dissolved mixture to produce a second mixture; washing the second mixture with an impurity remover to remove impurities and to produce an aconitic anhydride chloride solution; and mixing the docetaxel with the aconitic anhydride chloride solution to produce the drug-organic-acid-anhydride conjugate.

7 Claims, 11 Drawing Sheets

| Name | HPLC (RT; min) | Conjugation Site | Mw |
|---|---|---|---|
| DTX-AA$_3$ | 9.4 | A, B, C | 1,222 |
| DTX-AA$_2$ | 10.0 | A, B | 1084 |
| DTX-AA$_1$ | 10.6 | A | 946 |

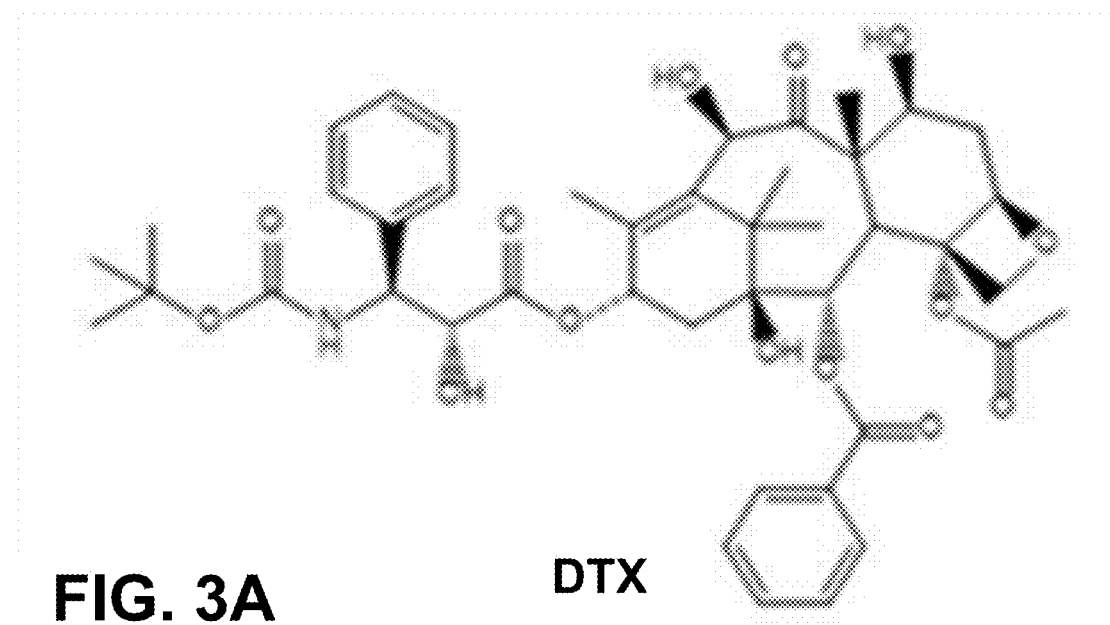
FIG. 3A DTX
MC ↓ TMS Protection
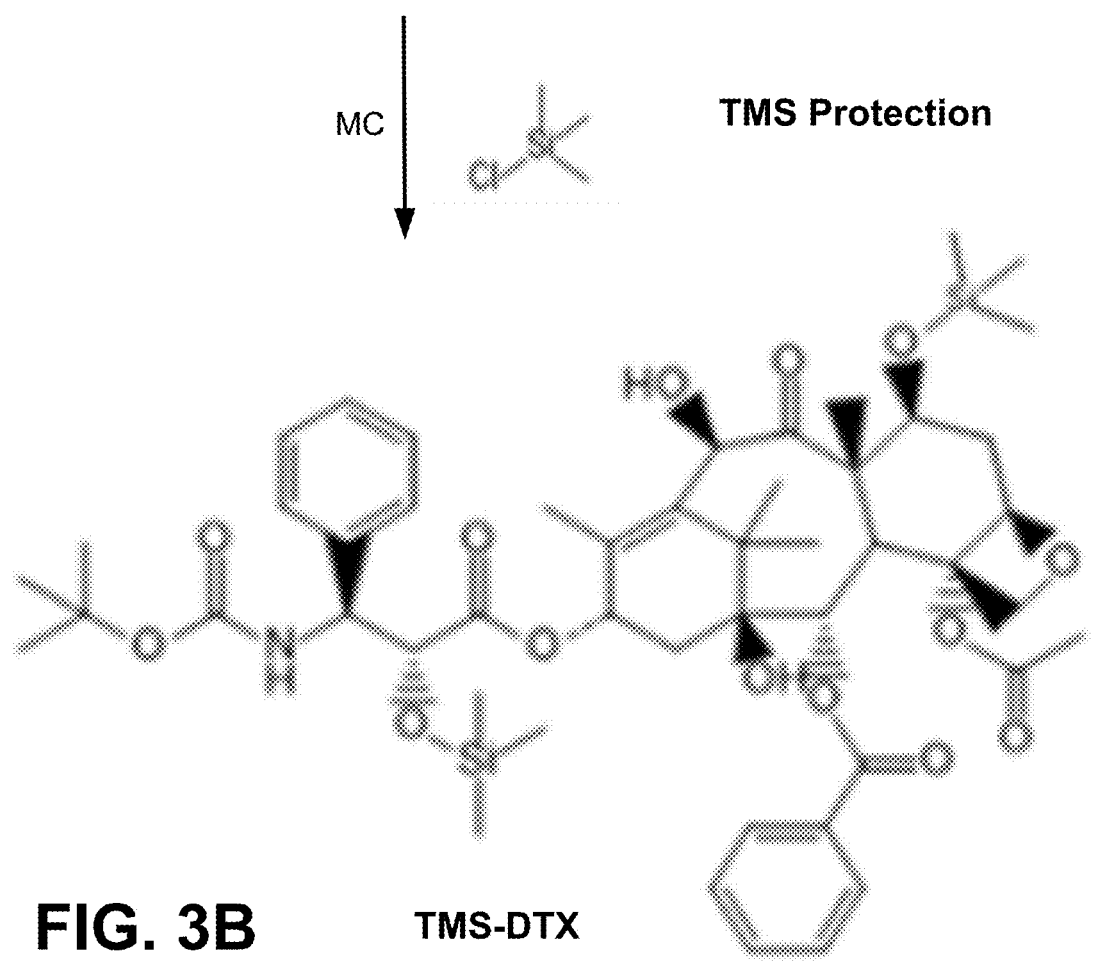
FIG. 3B TMS-DTX

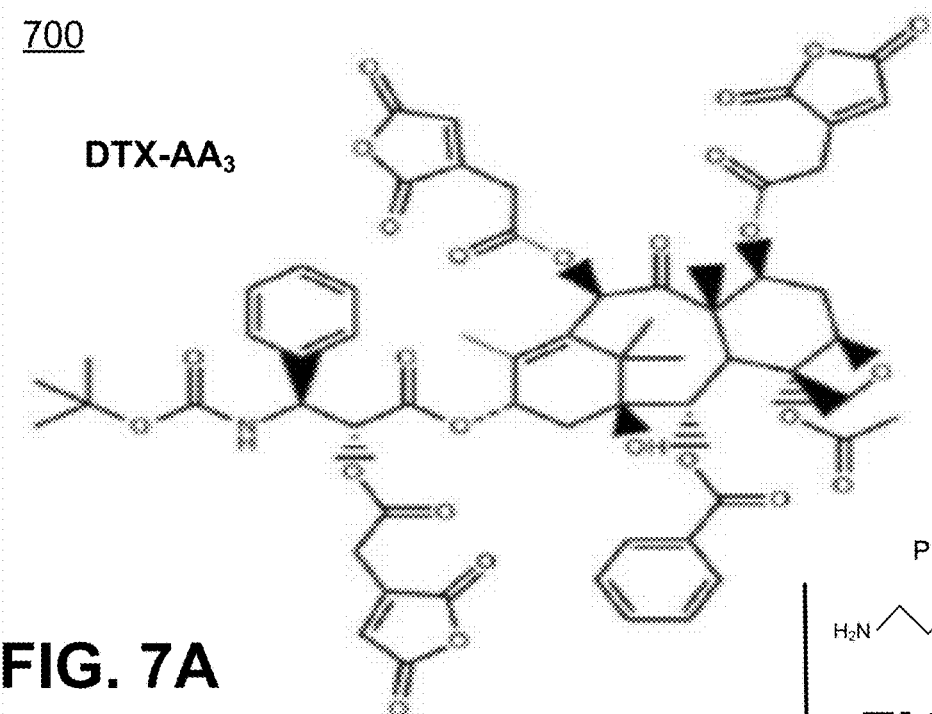
DTX-AA₃
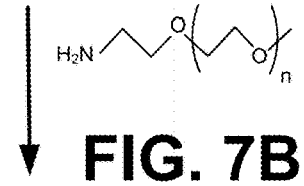
PEG-amine
FIG. 7A
FIG. 7B
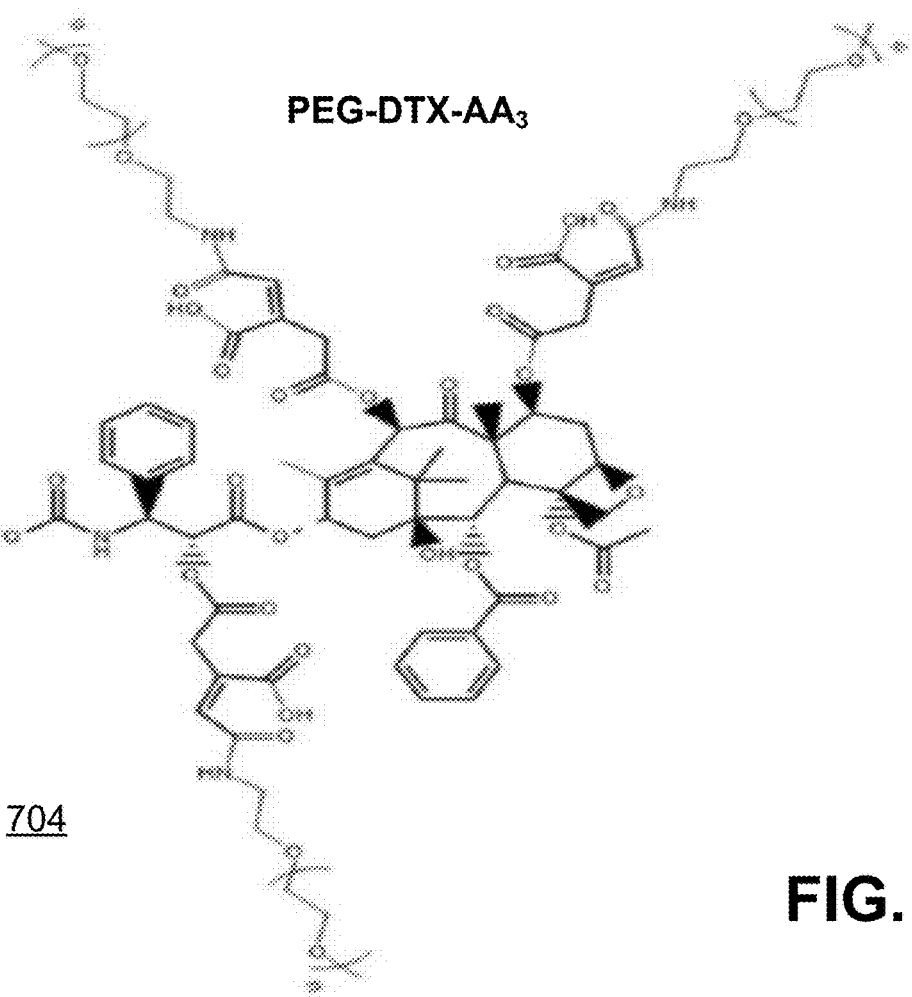
PEG-DTX-AA₃
FIG. 7C

SYNTHESIZING DRUG-ORGANIC-ACID-ANHYDRIDE CONJUGATES WITHOUT USING COUPLING REAGENT

CROSS-REFERENCE TO RELATED APPLICATIONS

This application claims the benefits of priority under 35 U.S.C. § 119(e) of: (1) U.S. Provisional Patent Application No. 63/009,312, filed Apr. 13, 2020; (2) U.S. Provisional Patent Application No. 63/030,103, filed May 26, 2020; (3) U.S. Provisional Patent Application No. 63/030,594, filed May 27, 2020; (4) U.S. Provisional Patent Application No. 63/037,474, filed Jun. 10, 2020; (5) U.S. Provisional Patent Application No. 63/037,477, filed Jun. 10, 2020; (6) U.S. Provisional Patent Application No. 63/038,444, filed Jun. 12, 2020; (7) U.S. Provisional Patent Application No. 63/043,579, filed Jun. 24, 2020; (8) U.S. Provisional Patent Application No. 63/045,518, filed Jun. 29, 2020; and (9) U.S. Provisional Patent Application No. 63/048,454, filed Jul. 6, 2020. The disclosures of the above-referenced applications are incorporated herein by reference.

BACKGROUND

Field

The present disclosure relates to synthesizing drug-organic acid anhydride conjugates, and more specifically, to synthesizing drug-organic acid anhydride conjugates without using coupling reagent.

Background

It is known that small molecule-based, naturally-derived substances and chemical-based drugs can temporarily bind to specific proteins through interactions of a 3-dimensional structure, namely hydrophobicity and hydrophilicity. Small molecule-based drugs, which account for 80% or more of currently used drugs, use these properties of small molecule substances, and play a role of inhibiting the function and activity of proteins in cells. Through this, it is possible to control the action of proteins (e.g., enzymes) in vivo and further treat diseases.

However, even small molecule drugs currently on the market need to improve and supplement various aspects such as drug efficacy, side effects, and physical properties in order to enhance patient convenience. To this end, studies are being conducted to try various chemical improvements using amine and hydroxy groups of small molecule drugs. For example, in the case of docetaxel, an anticancer agent, studies have been reported to chemically modify a hydroxy group to improve water-insoluble properties or to improve loading efficiency in microparticles.

SUMMARY

The present disclosure provides for removing a purification step of a coupling reagent by providing a method that allows chemical modification without the coupling reagent.

In one implementation, a method for synthesizing a drug-organic-acid-anhydride conjugate using docetaxel as a drug is disclosed. The method includes: mixing aconitic anhydride with a chlorinating reagent to produce a first mixture; dissolving the first mixture in an organic solvent to produce a dissolved mixture; stirring the dissolved mixture; evaporating the organic solvent from the dissolved mixture to produce a second mixture; washing the second mixture with an impurity remover to remove impurities and to produce an aconitic anhydride chloride solution; and mixing the docetaxel with the aconitic anhydride chloride solution to produce the drug-organic-acid-anhydride conjugate.

In another implementation, a method for synthesizing a polyethylene-glycol docetaxel-aconitic anhydride conjugate is disclosed. The method includes: mixing polyethylene-glycol amine with docetaxel-aconitic anhydride conjugate to produce a powder mixture; dissolving the powder mixture in a solvent to produce a dissolved mixture; stirring the dissolved mixture; evaporating the solvent from the dissolved mixture to produce a final mixture; and dispersing the final mixture in ether to produce the polyethylene-glycol docetaxel-aconitic anhydride conjugate.

Other features and advantages should be apparent from the present description which illustrates, by way of example, aspects of the disclosure.

BRIEF DESCRIPTION OF THE DRAWINGS

The details of the present disclosure, both as to its structure and operation, may be gleaned in part by study of the appended drawings, in which like reference numerals refer to like parts, and in which:

FIGS. 3A through 3E illustrate a method for the drug-OAH conjugate synthesis by linking the OAH and the drug with protection/deprotection in accordance with one implementation of the present disclosure;

FIGS. 7A through 7C illustrate the structure of $DTX-AA_3$ conjugated to PEG-amine to produce $PEG-DTX-AA_3$ in accordance with one implementation of the present disclosure;

DETAILED DESCRIPTION

Figure 1A:
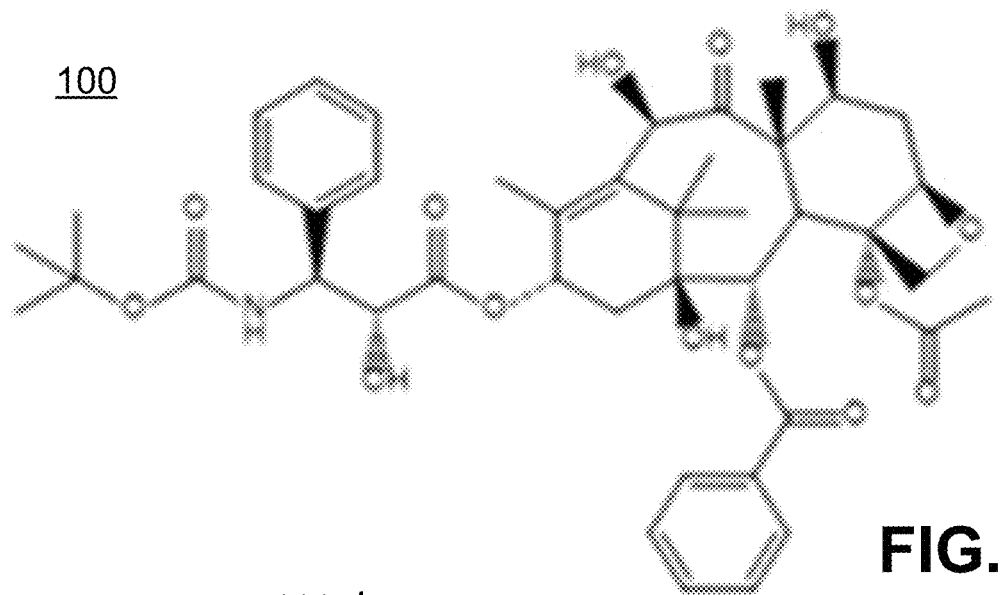
FIGS. 1A through 1C show a drug-OAH conjugate synthesis process linking the drug and OAH to produce the drug-OAH conjugate in accordance with one implementation of the present disclosure.

As noted above, since small molecule drugs currently on the market need to improve and supplement various aspects such as drug efficacy, side effects, and physical properties, studies are being conducted to try various chemical improvements using amine and hydroxy groups of small molecule drugs. Conventional methods involved adding chemical substances such as coupling reagents for chemical modification, and thus there was a need to remove them through an additional purification afterwards.

Certain implementations of the present disclosure include removing the purification step of the coupling reagent by providing a method that allows chemical modification without a coupling reagent. In one implementation, a small molecule drug is chemically modified ("small molecule drug derivative") through an acylation method. Cell and animal experiments have confirmed that the efficacy of the original drug is maintained but the toxicity is remarkably decreased by using the small molecule drug derivative alone. Further, when the small molecule drug derivative is combined with a hydrophilic polymer, the physical properties are improved, such that the solubility in water for injection and buffer solution is increased, and the "long blood circulation" (a well-known property of polymer-based nanomaterials) is possible. Term "long blood circulation" is used to describe the extended blood-circulation time of the polymer-based nanomaterials by reducing their mononuclear phagocytic system (MPS) uptake due to the polymer. Accordingly, using the above-described characteristics, oral, intravenous injection (infusion), and subcutaneous injection formulations may be applied to diseases caused by abnormal cell proliferation and infection, such as cancer and viral infections, either alone or through combination therapy. In one implementation, a method for synthesizing a drug-organic-acid-anhydride (drug-OAH) conjugate without using a coupling reagent is described. This method provides the convenience for purification.

In another implementation, a method for synthesizing the pharmaceutical composition (i.e., the drug-OAH) to maintain the efficacy of the drug with reduced toxicity to reduce the side effect is described. In one implementation, the pharmaceutical composition is used alone. In another implementation, the pharmaceutical composition is used through combination therapy.

In yet another implementation, the pharmaceutical composition is formulated for intravascular injection, oral administration or subcutaneous injection, by linking to polymers, antibodies, and nano- and/or micro-particles.

In a further implementation, the pharmaceutical composition is chemically bound to a hydrophilic or amphiphilic polymer (e.g., polyethylene-glycol (PEG) amine (PEG-amine)) and a pH-sensitive, biodegradable polymer.

After reading the descriptions recited in this section, it will become apparent how to implement the disclosure in various implementations and applications. Although various implementations of the present disclosure will be described herein, it is understood that these implementations are presented by way of example only, and not limitation. As such, the detailed description of various implementations should not be construed to limit the scope or breadth of the present disclosure.

As described above, the pharmaceutical composition (i.e., the drug-OAH) is a conjugate compound in which the drug (D) is bound to the organic-acid-anhydride (OAH).

In one implementation, D may be one selected from the below-listed compounds (including a hydroxyl or primary amine group), but is not limited thereto. Further, D may include drugs with high toxicity, which limit the dose concentration due to the necessity of highly controlling toxicity, such as anticancer agents. In another implementation, D may include drugs that are hydrophobic and are highly necessary to improve their physical properties. The list includes: (a) Taxane-based drugs such as paclitaxel or docetaxel, colchicine analogs (microtubule inhibitors), and in addition to those, a naturally-derived substance that inhibits a division of cells by binding to tubulin present in a cell; (b) Platinum compounds such as cisplatin, carboplatin, nedaplatin, and other similar compounds; (c) Deoxyribonucleic Acid (DNA) intercalating agent such as mitoxantrone; (d) Anthracycline-based drugs such as doxorubicin, idarubicin, etc., and other than those, drugs which block cell growth and division by directly binding to the DNA to destroy the molecule itself and damage the same or double helix structure of the DNA; (e) The DNA synthesis inhibitors such as methotrexate (MTX), etc., and other than those, drugs that interfere with the action by competitively binding with normal metabolites to the enzymes of biosynthesizing purine and pyrimidine, which are constituents of DNA and RNA; (f) Topoisomerase I inhibitor such as camptothecin, and other similar inhibitors; (g) Endocytosis inhibitor such as hydroxychloroquine, and other similar inhibitors; (h) Protease inhibitor such as nafamostat, and other similar inhibitors; and (i) Drugs which were proven as having anti-virus effect against reterovirus such as niclosamide, cyclosporine, perhexiline maleate, loperamide, mefloquine, amodiaquine, proscillaridin, phenazopyridine, digitoxin, penfluridol, clomiphene, toremifene, digoxin, hexachlorophene, hydroxyprogesterone, thioridazine, salinomycin, quinacrine, eltrombopag, cepharanthine, ciclesonide, oxyclozanide, LDK378, dihydrogambogic acid, osimertinib (AZD-9291), isopomiferin, anidulafungin (LY303366), osajin, lusutrombopag, isoosajin, gilteritinib, berbamine, ebastine, tetrandrine, abemaciclib (USAN), ivacaftor, bazedoxifene, mequitazine, triparanol, droloxifene, dronedarone, lopinavir, favipiravir, atazanavir, and other similar drugs.

In another implementation, OAH may be one selected from the compounds listed below, but is not limited thereto. The list includes: (a) Aconitic anhydride and aconitic acid derived compounds; (b) Succinic anhydride and succinic acid derived compounds; (c) Glutaric anhydride and glutaric acid derived compounds; (d) Citric anhydride and citric acid derived compounds; (e) Maleic acid derivative such as 1-methyl-2-(20-carboxyethyl) maleic anhydride (MCM), carboxylate dimethyl maleic anhydride (CDM), and other similar derivatives; and (f) Other anhydrides of polyhydric organic acids and derivatives thereof.

As stated above, the pharmaceutical composition may be used alone, but synergistic drug effects may be achieved through combination therapy of the above-listed drug with the conjugate compound which is bound to the drug (i.e., the OAH). In one implementation, a docetaxel/aconitic anhydride conjugate compound and a cisplatin/succinic anhydride conjugate compound may be used in combination to maximize the anticancer efficacy. In another implementation, a hydroxychloroquine/glutaric anhydride conjugate compound and a mitotrexate/aconitic anhydride conjugate compound may be used in combination to maximize the antiviral efficacy.

In one implementation, the pharmaceutical compositions and derivatives (e.g., conjugation compounds with polymers) can be developed as drugs through following formulations.

(a) In the cases of intravascular and subcutaneous injections: (1) Micelle formulation using amphipathic polymers such as polyethylene glycol poly-lactide-co-glycolide (PEG-PLGA) and polyethylene glycol-b-poly L-lysine (PEG-PLL); (2) Formulation using surfactants such as Tween 80, and organic solvent such as ethanol; (3) Sustained releasing formulation through binding of pH sensitive or degradable polymers; and (4) Polymer-drug-OAH conjugate compounds prepared by conjugation with drugs having amine groups such as PEG-amine and PLL.

(b) In the case of oral administration: (1) Formulations containing enteric coating agents including polymers such as Eudragit, PEG or poloxamers); (2) Formulations containing polysaccharide-based substances such as starch and dextran; (3) Sustained-release formulation through a pH-sensitive or degradable polymer mixture; and (4) Substances including, trietyl citrate, hydroxypropyl methylcellulose (HPMC), cellulose acetate succinate, carboxyvinyl polymer such as carbomer, cellulose acetate phthalate, carboxymethyl cellulose, cellulose acetate phthalate, hydroxypropyl cellulos, ethyl cellulose, methyl cellulose, polyvinyl acetate phthalate, polyvinyl alcohol (PVA), can be used as additives to make the above formulations.

(c) In order to control a release of drugs and prevent a degradation, depending on the route of administration, there are plasticizer, solubilizing agent, sweetener agent, gelling agent, bonding agent, hardener, surfactant, anticaking agent, brightener, flavors enhancer, base, sugar coating agent, bulking agent for freeze-drying, isotonic agent, effervescent agent, desiccant, release-modifying agent, antimicrobial preservative, anti-adherent, filler, diluent, disintegrant, acidifying agent, oxidizer, osmotic regulator, sustained release modifying agent, cleanser, antifoaming agent, humectant, stabilizing agent, alkalizing agent, antioxidant, suspending agent, glidant agent, pH modifier, enteric coating agent such as Eudragit.

In one implementation, a list of diseases to be treated with the pharmaceutical composition alone or through a mixture of two or more including the following:

(a) Diseases caused by bacterial and viral infections including: (1) Infectious diseases including viral infection, malaria infection, and bacterial infection; virus disease including Epstein Barr virus (EBV), hepatitis B virus, hepatitis C virus, HIV, HTLV 1, varicella-zoster virus (VZV), and human papilloma virus (HPV); and (2) Corona virus infections such as SARS-CoV1 and SARS-CoV2, other retrovirus infections;

(b) Inflammatory disease including: (1) Vascular restenosis; and (2) Inflammatory diseases including autoimmune diseases, pancreatitis, glomerular nephritis, myocardial infarction, and psoriasis, allergic asthma, atopic dermatitis (eczema), and atopic disease (atopy) including allergic rhinitis; (3) cell mediated hypersensitivity, including allergic contact dermatitis and hypersensitivity pneumonitis; (4) rheumatic diseases including Systemic Lupus Erythematosus (SLE), rheumatoid arthritis, juvenile arthritis, Sjogren's syndrome, scleroderma, polymyositis, Ankylosing Spondylitis and psoriatic arthritis; (5) diabetes, autoimmune thyroid diseases, brain diseases, including dementia, Parkinson's disease, Alzheimer's disease, and other autoimmune diseases; (6) viral diseases including Epstein Barr virus (EBV), hepatitis B virus, hepatitis C virus, HIV, HTLV 1, varicella-zoster virus (VZV), and human papilloma virus (HPV); and (7) degenerative diseases including prion infection, Creutzfeldt-Jakob disease, and arthritis; and (c) Malignant tumor such as cancer including fibrosarcoma, myxosarcoma, liposarcoma, chondrosarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonic carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, and carcinoma created in breast, prostate, kidney, bladder, or colon tissue; tumor diseases appearing in adipose tissue, such as adipose cell tumors, e.g., lipoma, fibrolipoma, lipoblastoma, lipomatosis, hibemoma, hemangioma, and/or liposarcoma.

Figure 1B:
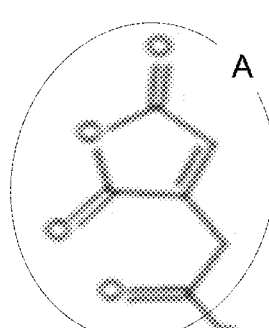
Figure 1C:
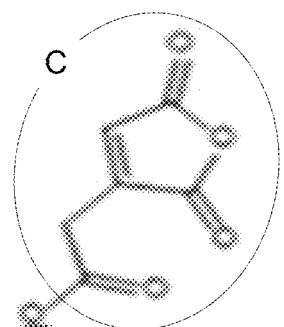
Figure 1C:
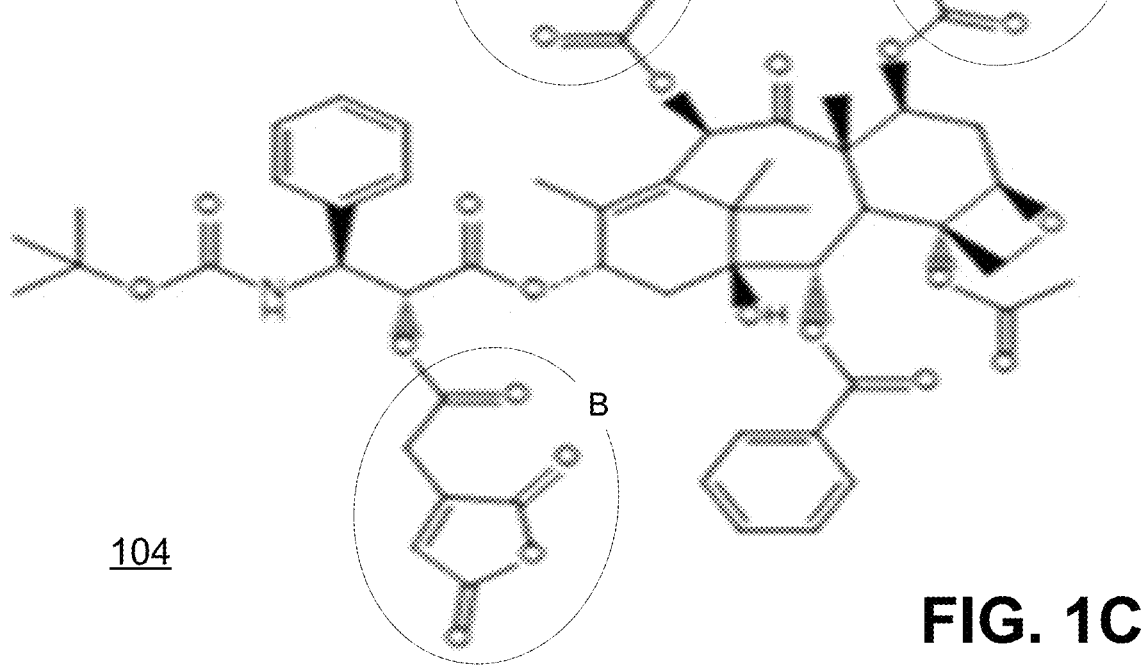

FIGS. 1A through 1C show a drug-OAH conjugate synthesis process linking the drug (e.g., docetaxel 100) and OAH (e.g., aconitic anhydride 102) to produce the drug-OAH conjugate (e.g., docetaxel-aconitic anhydride conjugate 104) in accordance with one implementation of the present disclosure. In one implementation, the method of synthesizing the drug-OAH includes following steps.

(a) Mix aconitic anhydride 102 with a chlorinating reagent, including phosphorus pentachloride ($PCl_3$), thionyl chloride, and oxaly chloride, phosphorus pentachloride ($PCl_3$). The term 'mix' refers to drop-wise addition of the chlorinating reagent.

(b) Dissolve the mixture from step (a) above in a solvent, including methylene chloride, chloroform, tetrahydrofuran (THF). In some cases, the solvent may be an organic solvent.

(c) Stir the dissolved mixture for approximately 1 to 2 hours.

(d) Evaporate the solvent (e.g., using rotary evaporator at room temperature) from the mixture to produce a second mixture. In some cases, the solvent may be an organic solvent.

(e) Wash the second mixture with an impurity remover, including cyclohexane, hexane, and ether, to remove certain impurities based on the solubility of the solvent (e.g., remnant organic solvent such as methylene chloride and un-reacted chlorinating reagent) and to produce the aconitic anhydride chloride (AACl) solution. In one implementation, the mixture is dispersed in cyclohexane, and the cyclohexane is then centrifuged and decanted to remove the impurities.

(f) Mix docetaxel and the produced AACl solution to produce a docetaxel-aconitic anhydride conjugate. In one implementation, the conjugate is produced by adding the produced AACl solution in methylene chloride or THF. In one implementation, various docetaxel-aconitic anhydride conjugates may be produced by varying the molar ratio between docetaxel and AACl from 1:1 to 1:4.5.

(e.g., docetaxel 100) and OAH (e.g., aconitic anhydride 102) to produce the drug-OAH conjugate (e.g., docetaxel-aconitic anhydride conjugate 104)

Figure 1D:
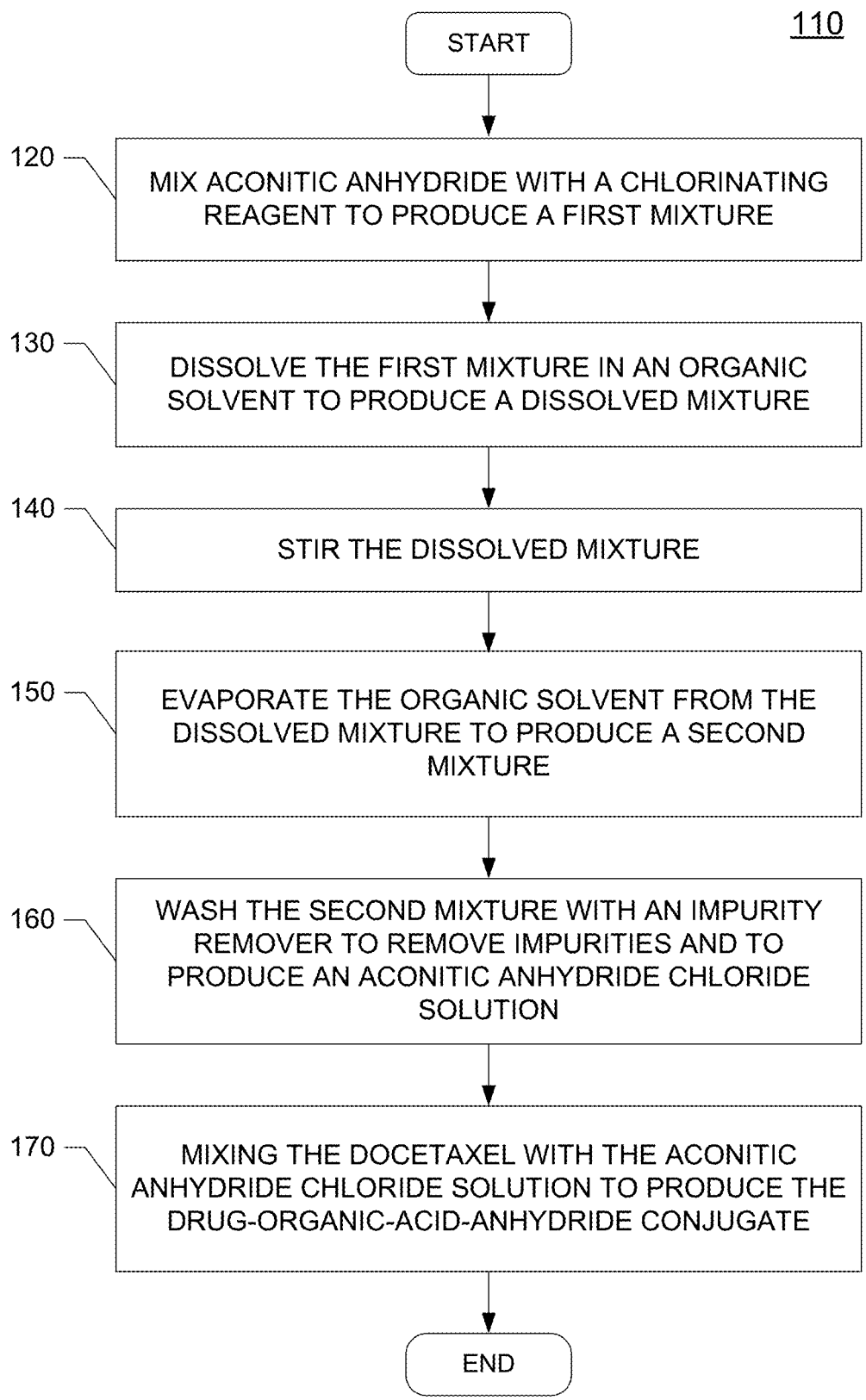
FIG. 1D is a flow diagram illustrating a method for synthesizing a drug-organic-acid-anhydride conjugate using docetaxel as a drug.

FIG. 1D is a flow diagram illustrating a method 110 for synthesizing a drug-organic-acid-anhydride conjugate using docetaxel as a drug. In the illustrated implementation of FIG. 1D, aconitic anhydride 102 is mixed with a chlorinating reagent, at block 120, to produce a first mixture. The first mixture is dissolved in an organic solvent, at block 130, to produce a dissolved mixture, and the dissolved mixture is stirred, at block 140. The organic solvent is then evaporated from the dissolved mixture, at block 150, to produce a second mixture. The second mixture is washed with an impurity remover, at block 160, to remove impurities and to produce an aconitic anhydride chloride solution. The docetaxel is mixed with the aconitic anhydride chloride solution, at block 170, to produce the drug-organic-acid-anhydride conjugate 104.

In one implementation, the chlorinating reagent includes phosphorus pentachloride. In one implementation, mixing the aconitic anhydride with the chlorinating reagent includes drop-wise adding the chlorinating reagent to the aconitic anhydride. In one implementation, stirring the dissolved mixture includes stirring the dissolved mixture for approximately 1 to 2 hours. In one implementation, the solvent includes methylene chloride. In one implementation, evaporating the solvent includes evaporating the solvent using a rotary evaporator at room temperature. In one implementation, the impurity remover includes cyclohexane. In one implementation, washing the second mixture with the impurity remover includes dispersing the second mixture in the cyclohexane. In one implementation, the method 110 further includes centrifuging and decanting the cyclohexane to remove the impurities. In one implementation, the drug-organic-acid-anhydride conjugate is a docetaxel-aconitic anhydride conjugate. In one implementation, mixing the docetaxel with the aconitic anhydride chloride solution includes varying a molar ratio between the docetaxel and the aconitic anhydride chloride solution from 1:1 to 1:4.5. In one implementation, the impurities are removed based on solubility of the solvent. In one implementation, mixing the aconitic anhydride includes selectively conjugating the aconitic anhydride to a hydroxy group located at a specific position through selective chemical modification. In one implementation, the selective chemical modification is performed using a protecting group including trimethyl silane.

Figures 2A, 2B:
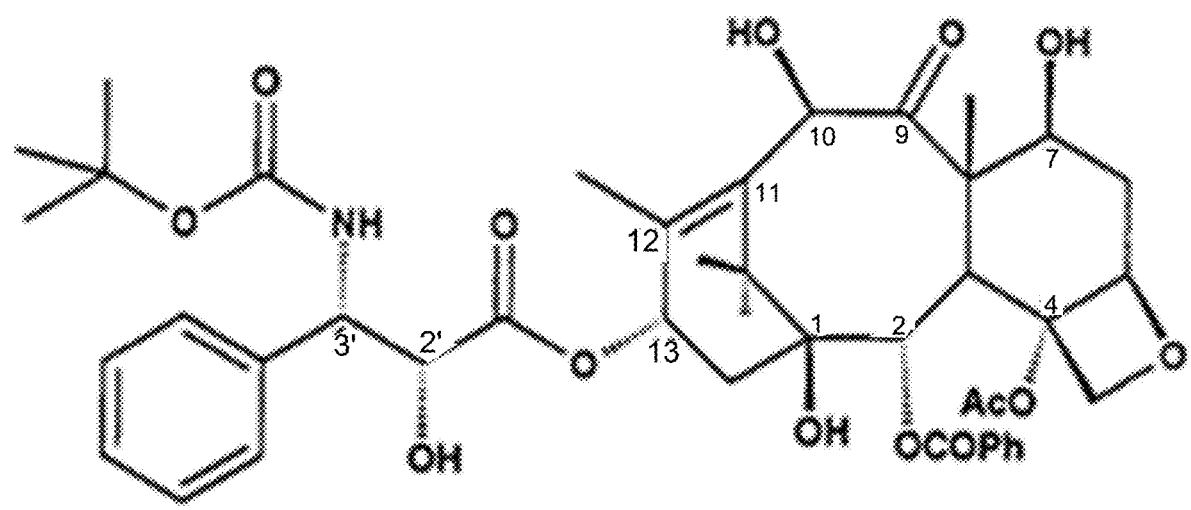
FIG. 2A shows a table of various forms of the drug-OAH conjugate separated through the high-performance liquid chromatography (HPLC) purification process in accordance with one implementation of the present disclosure.
FIG. 2B shows the chemical structure of the docetaxel with positions labelled.

FIG. 2A shows a table of various forms of the drug-OAH conjugate separated through the high-performance liquid chromatography (HPLC) purification process in accordance with one implementation of the present disclosure. The table shows the various forms of the conjugate separated through the HPLC purification process after synthesis by linking the OAH (e.g., aconitic anhydride) and the drug (e.g., docetaxel). In one implementation, preparative scale HPLC may be conducted to collect specific fractions. Preparative fractions are typically collected by means of a diverter valve that can be triggered either by time settings or detector signal.

In one implementation, the synthesized Drug-OAH (e.g., docetaxel-Aconitic anhydride conjugate) includes below characteristics.

(a) When aconitic anhydride activated in the form of acyl chloride is conjugated to docetaxel, the site-specific modification is possible.

(b) In the case of docetaxel, the reactivity to the activated aconitic anhydride differs depending on the position of the hydroxy group. In one implementation, the reaction proceeds in the order of positions 10→2'→7. FIG. 2B shows the chemical structure of the docetaxel with positions labelled. It should be noted that positions 2', 7, 10-OH indicate the hydroxyl group connected to the carbon at 2'C, 7C, 10C positions indicated in FIG. 2B. The result of a study on the conjugation of cis-aconitic anhydride to docetaxel have revealed that cis-aconitic anhydride is conjugated first to the 10-OH group in DTX, rather than 2'-OH or 7-OH group. The second conjugation site of cis-aconitic anhydride to DTX moieties was 2'-OH group of DTX, while the last conjugation sites was 7-OH group. Thus, from the result, it can be concluded that the reactivity for the conjugation of cis-aconitic anhydride has a priority; 10-OH→*2'-OH→*7-OH. However, it is possible for the priority to be affected/changed by the surrounding chemical environment (i.e., steric hindrance).

(c) Thus, according to FIG. 2A, three different types of drug-OAH conjugates can be obtained depending on where the aconitic anhydride was attached. Type 1 includes all three OAHs attached. Type 2 includes two OAHs attached. Type 3 include only one OAH attached.

In one implementation, the mass production process for drug-OAH (e.g., docetaxel-Aconitic anhydride conjugate) is developed as described below.

Figures 3C, 3D, 3E:
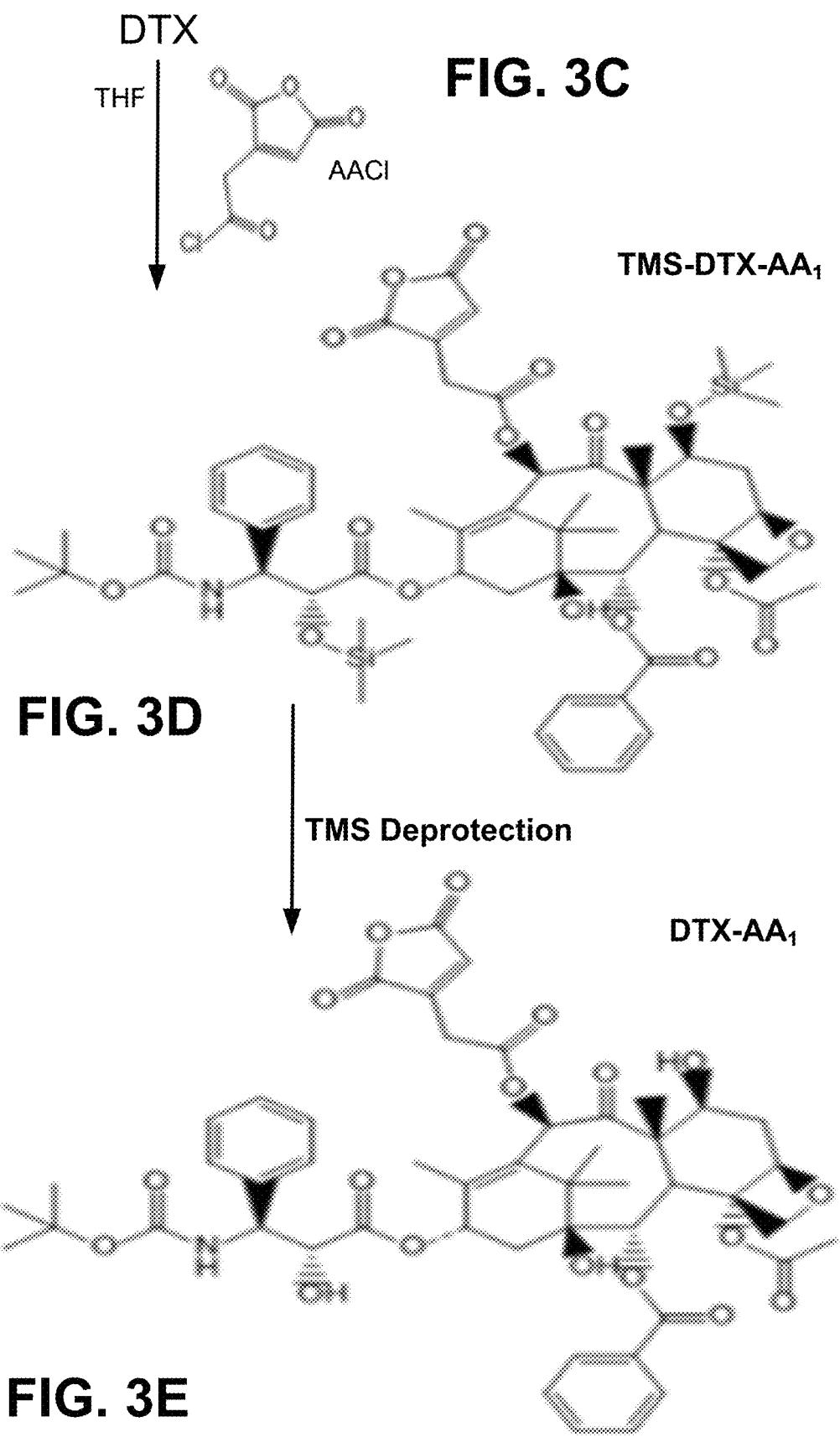

FIGS. 3A through 3E illustrate a method for the drug-OAH conjugate (DTX-AA$_1$) synthesis by linking the OAH (e.g., aconitic anhydride) and the drug (e.g., docetaxel) with protection/deprotection in accordance with one implementation of the present disclosure. As shown in FIGS. 3A and 3B, for the selective conjugation of aconitic anhydride to 10-OH position, trimethyl silane (TMS) is conjugated to 2'-OH and 7-position. Differently with aconitic anhydride, TMS has a priority in chemical conjugation on 2'-OH and 7-OH than 10-OH. As shown in FIGS. 3C and 3D, aconitic anhydride is conjugated using AACl on the empty 10-OH. Subsequently, as shown in FIG. 3E, TMS groups were deprotected to obtain docetaxel-aconitic anhydride conjugate (DTX-AA$_1$).

In the illustrated implementation of FIGS. 3A through 3E, the aconitic anhydride could be selectively conjugated to a hydroxy group located at a specific position through selective chemical modification or protection using a protecting group such as TMS. When using a method such as the chemical protection, there is no need to use a purification method such as preparative HPLC (prep-HPLC). HPLC is generally used to separate specific chemical compounds from a mixed solution after a synthesis reaction or from natural extracts, while the prep-HPLC is used to fraction high-purity compounds required for subsequent evaluation and analysis. Thus, without the need for a purification step, the mass production is possible.

Figure 4:
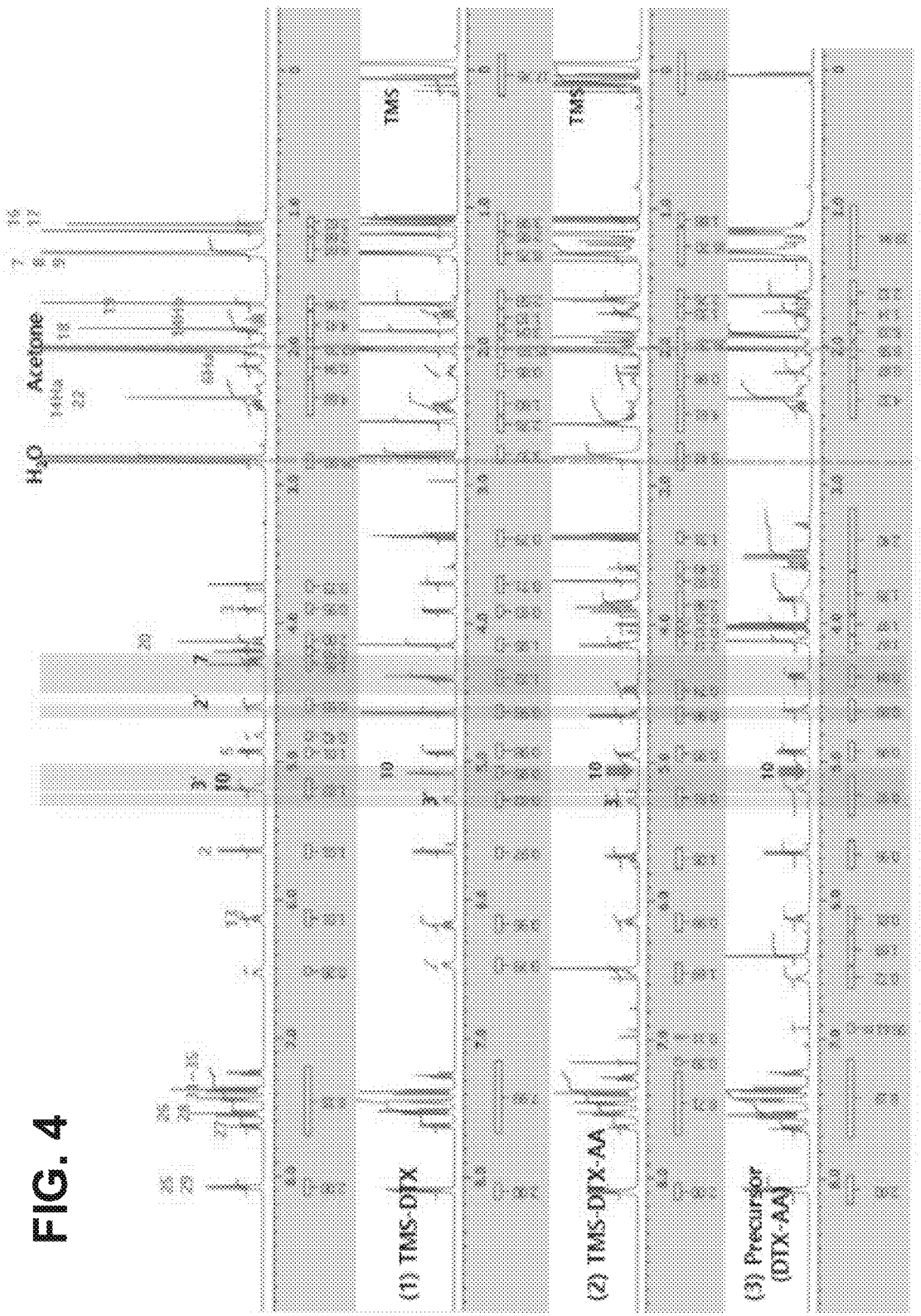
FIG. 4 illustrates the proton nuclear magnetic resonance analysis result of the $DTX-AA_1$ synthesized by linking OAH and drug with protection/deprotection in accordance with one implementation of the present disclosure.

FIG. 4 illustrates the proton nuclear magnetic resonance (proton NMR, hydrogen-1 NMR, or $^1$H-NMR) analysis result of the DTX-AA$_1$ synthesized by linking OAH (e.g., aconitic anhydride) and drug (e.g., docetaxel) with protection/deprotection in accordance with one implementation of the present disclosure. In the illustrated implementation of FIG. 4, the $^1$H-NMR result confirms that aconitic anhydride is conjugated at a specific location. The $^1$H chemical shift for the hydrogens connected to C-2' (4.62 ppm), C-7 (4.28 ppm) and C-10 (5.20 ppm) atoms resonated at down-field of $^1$H-NMR spectra due to the conjugation. For example, as shown in FIG. 4, the $^1$H-NMR for 1 cis-aconityl DTX verifies the conjugation of cis-aconitic anhydride to the OH group at the C-10 atom, by the absence of the peak at 5.20 ppm and its shift to 6.52 ppm.

Figure 5:
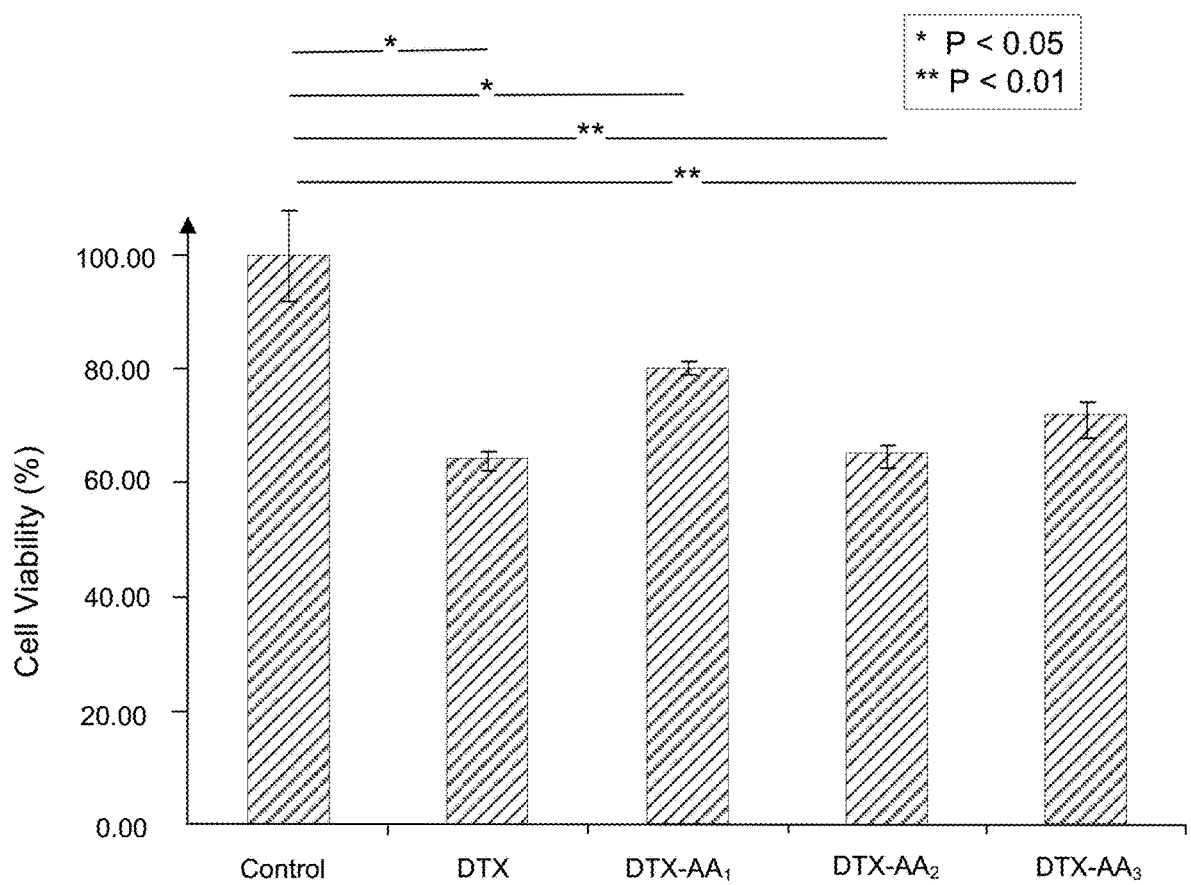
FIG. 5 illustrates the anticancer efficacy result of the drug-OAH conjugate made by linking docetaxel and aconitic anhydride in the cell experiment in accordance with one implementation of the present disclosure.

FIG. 5 illustrates the anticancer efficacy result of the drug-OAH conjugate made by linking docetaxel and aconitic anhydride in the cell experiment in accordance with one implementation of the present disclosure. The illustrated implementation of FIG. 5 shows that the drug-OAH conjugate maintains the anticancer efficacy of docetaxel, which shows the effective cancer cell killing effect. In FIG. 5, the statistical significance indicates that a result from data generated by the testing is not likely to occur randomly or by chance but is instead likely to be attributable to a specific cause. P value has been used to evaluate the statistical significance, wherein if the P value falls below the significance level, then the result is statistically significant. That is, in FIG. 5, the P value less than 0.05 is 'significant'. The p-value is a function of the means and standard deviations of the data samples. In FIG. 5, the bars on the graph refer to error bars and the asterisks refers to the significance. Small error bars and asterisks represent that the experimental result is reliable.

Figure 6A:
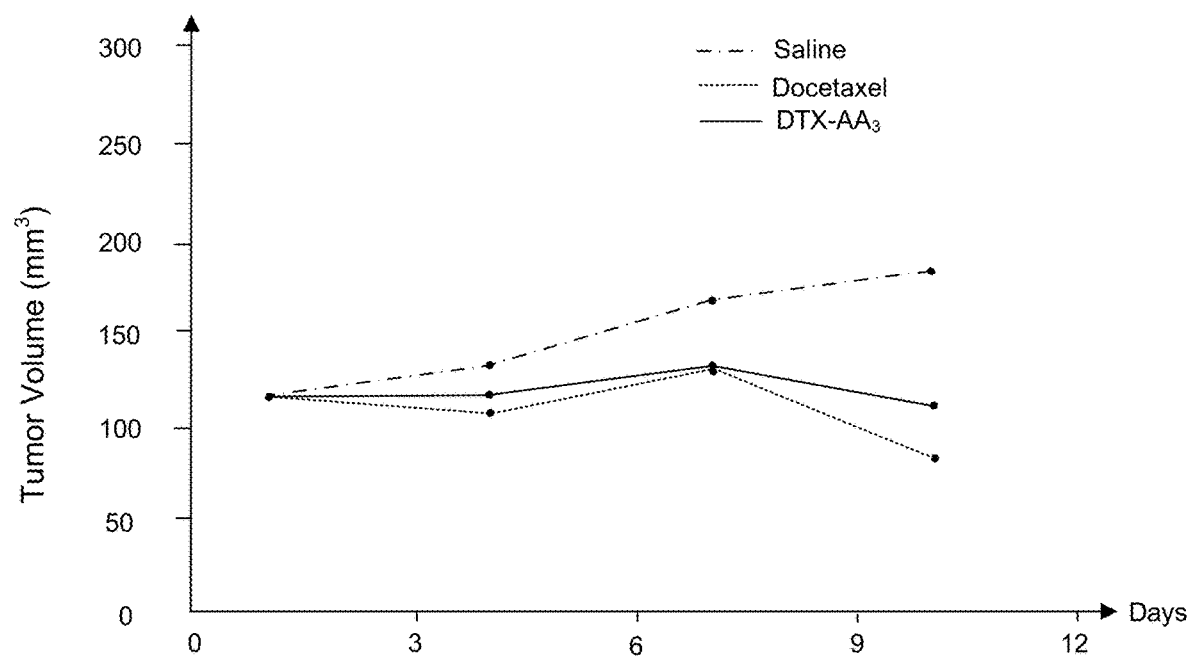
FIGS. 6A and 6B illustrate the anticancer efficacy result of the drug-OAH conjugate made by linking docetaxel and aconitic anhydride in the animal experiment in accordance with one implementation of the present disclosure.
Figure 6B:
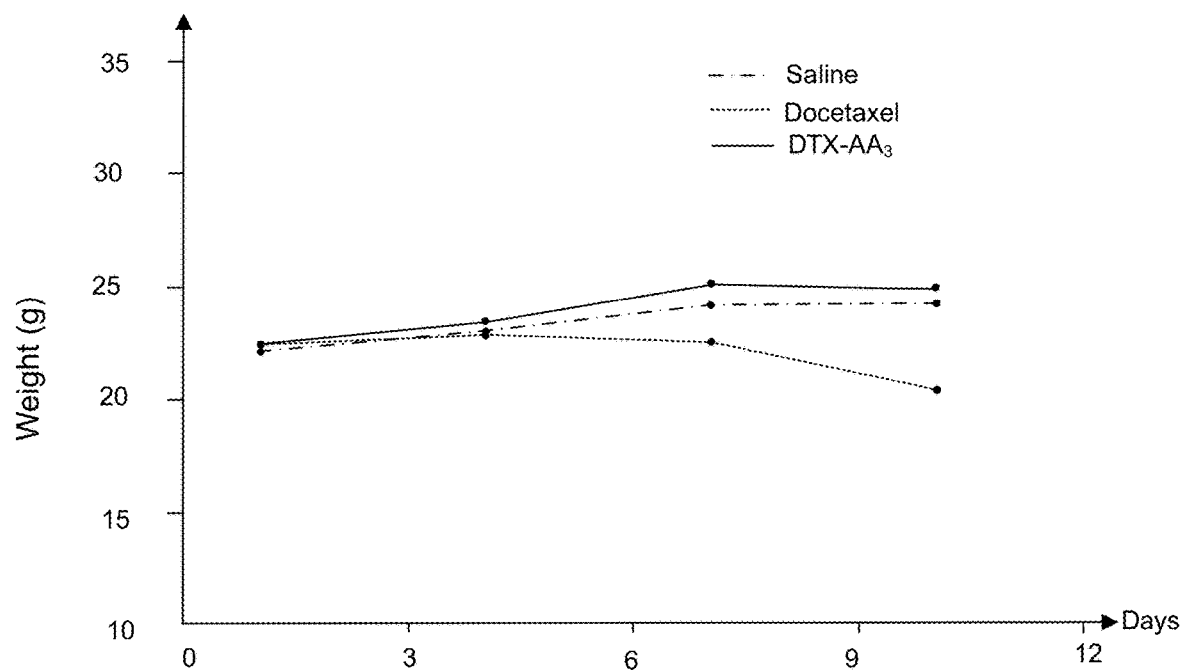

FIGS. 6A and 6B illustrate the anticancer efficacy result of the drug-OAH conjugate made by linking docetaxel and aconitic anhydride in the animal experiment (i.e., the mouse xenograft model) in accordance with one implementation of the present disclosure. The graphs show that the conjugate possesses the anti-cancer efficacy such as the starting material, docetaxel. Normally, non-treated group is injected with saline (NaCl solution) in anti-cancer efficacy study. The drug-OAH conjugate treatment group shows similar anti-cancer effects to docetaxel, and no weight loss was observed (dose: DTX standard, 20 mg/kg). Thus, the result of the animal experiment shows that the docetaxel-aconitic anhydride conjugate maintains the anticancer efficacy of docetaxel without the observed weight loss.

The toxic reduction effect of the drug-OAH (e.g., docetaxel-aconitic anhydride conjugate ($DTX-AA_3$)) may be analyzed as follows:

(a) Docetaxel-aconitic anhydride conjugate is administered to the mice and tested every hour up to 6 hours after administration on the day of administration, and once a day or more from day 1 to day 14 after administration. The symptoms that may appear due to the administration of the test substance were observed (e.g., changes in the general condition, the development of the addiction symptom, and the presence or absence of the dead animals). The results showed that no specific symptoms appeared. Therefore, all animals used in this test were considered to be healthy during the two-week test period; and (b) No dead animals resulted in all male and female mouse animal groups including the highest dose group throughout the test period.

FIGS. 7A through 7C illustrate the structure of $DTX-AA_3$ (see 700 shown in FIG. 7A) conjugated to PEG-amine (see 702 shown in FIG. 7B) to produce $PEG-DTX-AA_3$ (see 704 shown in FIG. 7C) in accordance with one implementation of the present disclosure. In a first implementation, the structure of $PEG-DTX-AA_3$ 704 represents a formulation for intravascular injection. In a second implementation, the structure of $PEG-DTX-AA_3$ 704 represents an oral formulation.

In the first implementation (i.e., intravascular injection), conjugating the polyphosphazene compound (wherein the branch group is substituted with polylysine and PEG) to $DTX-AA_1$ (which produces $PEG-DTX-AA_3$), the result indicates that the solubility in aqueous solutions, such as water for injection, was improved (100 mg/mL). The result also indicates that the changes of the pharmacokinetics (PK) profile due to the long blood circulation were observed.

In the first implementation (i.e., intravascular injection), conjugating $DTX-AA_3$ 700 to PEG-amine 702, the result showed improvement in solubility in aqueous solutions such as water for injection. The result also indicated that the changes of the PK profile due to the long blood circulation were observed.

Figure 8:
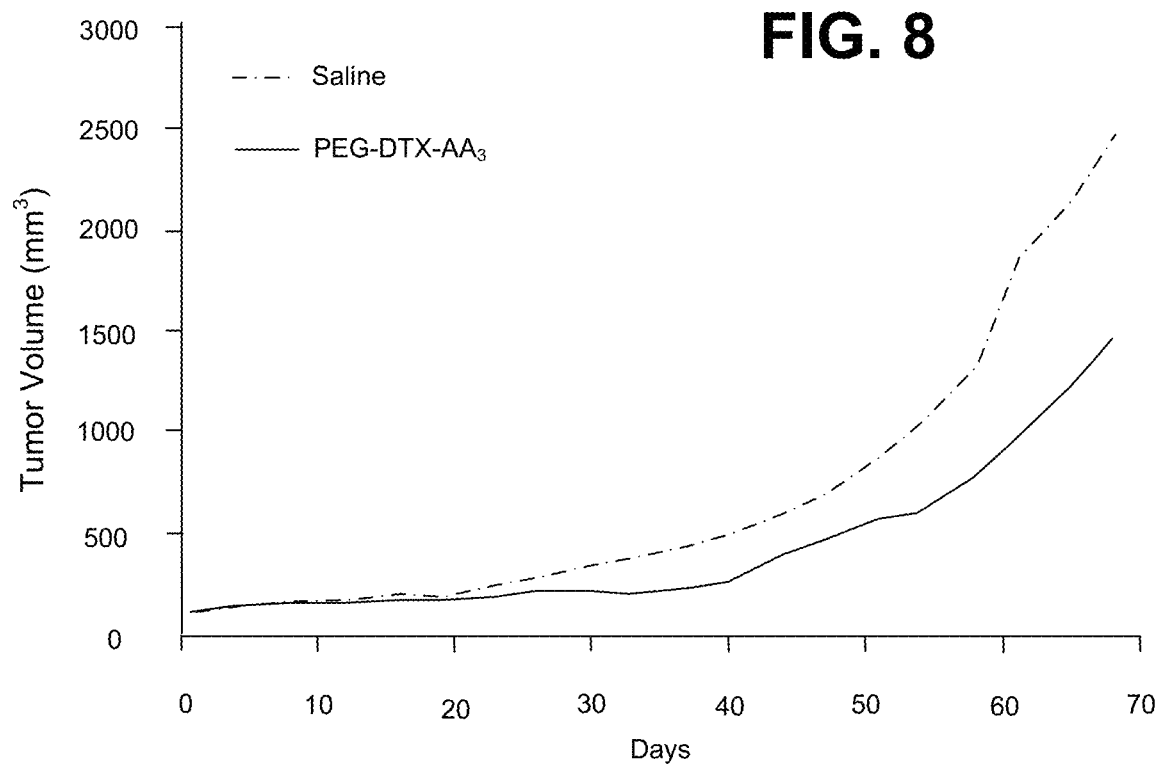
FIG. 8 illustrates the anticancer efficacy result for $PEG-DTX-AA_3$.

FIG. 8 illustrates the anticancer efficacy result for $PEG-DTX-AA_3$.

In the second implementation (i.e., oral formulation), a tablet formulation was prepared by mixing lactose powder, hydroxypropyl cellulose and $DTX-AA_3$. The prepared tablet formulation was disintegrated under the standard drug release conditions to release $DTX-AA_3$. In one implementation, a substance with chemically improved structure of $DTX-AA_3$ 700 can also be prepared in an oral dosage form, and released after disintegration is observed.

Figure 9:
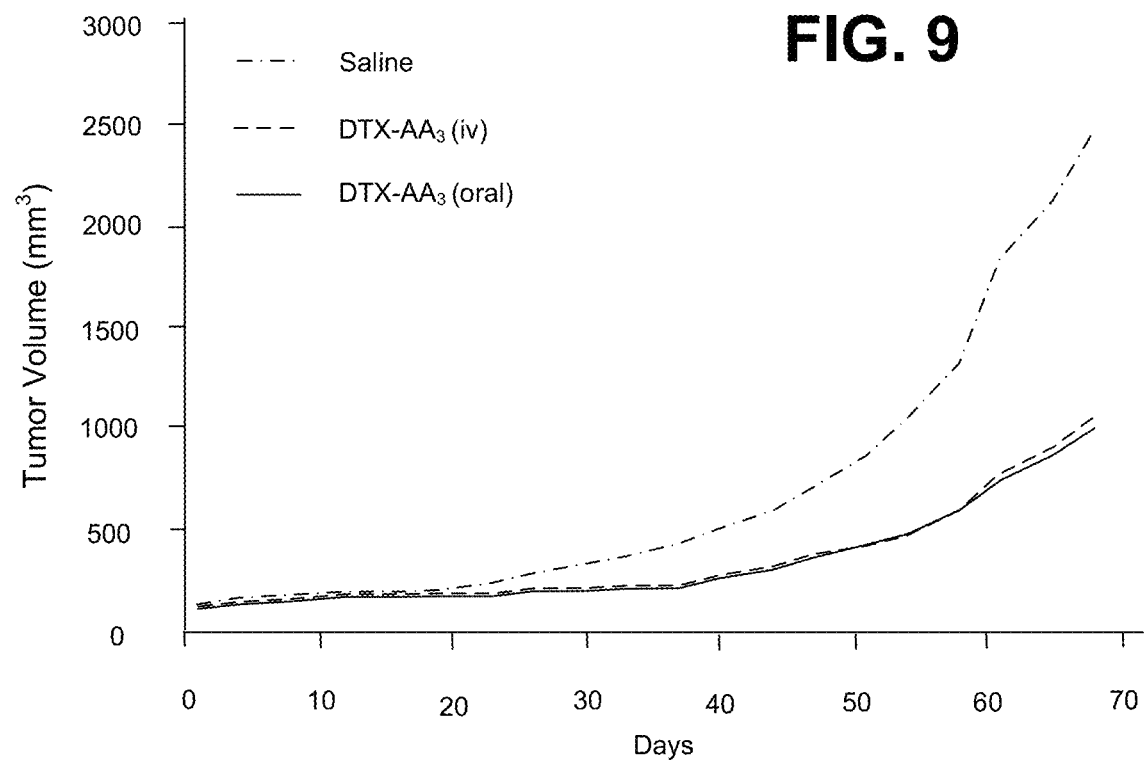
FIG. 9 illustrates the comparison of the anticancer efficacy results of $DTX-AA_3$ administered orally and by intravenous method.

FIG. 9 illustrates the comparison of the anticancer efficacy results of $DTX-AA_3$ 700 administered orally and by intravenous method.

Figure 10:
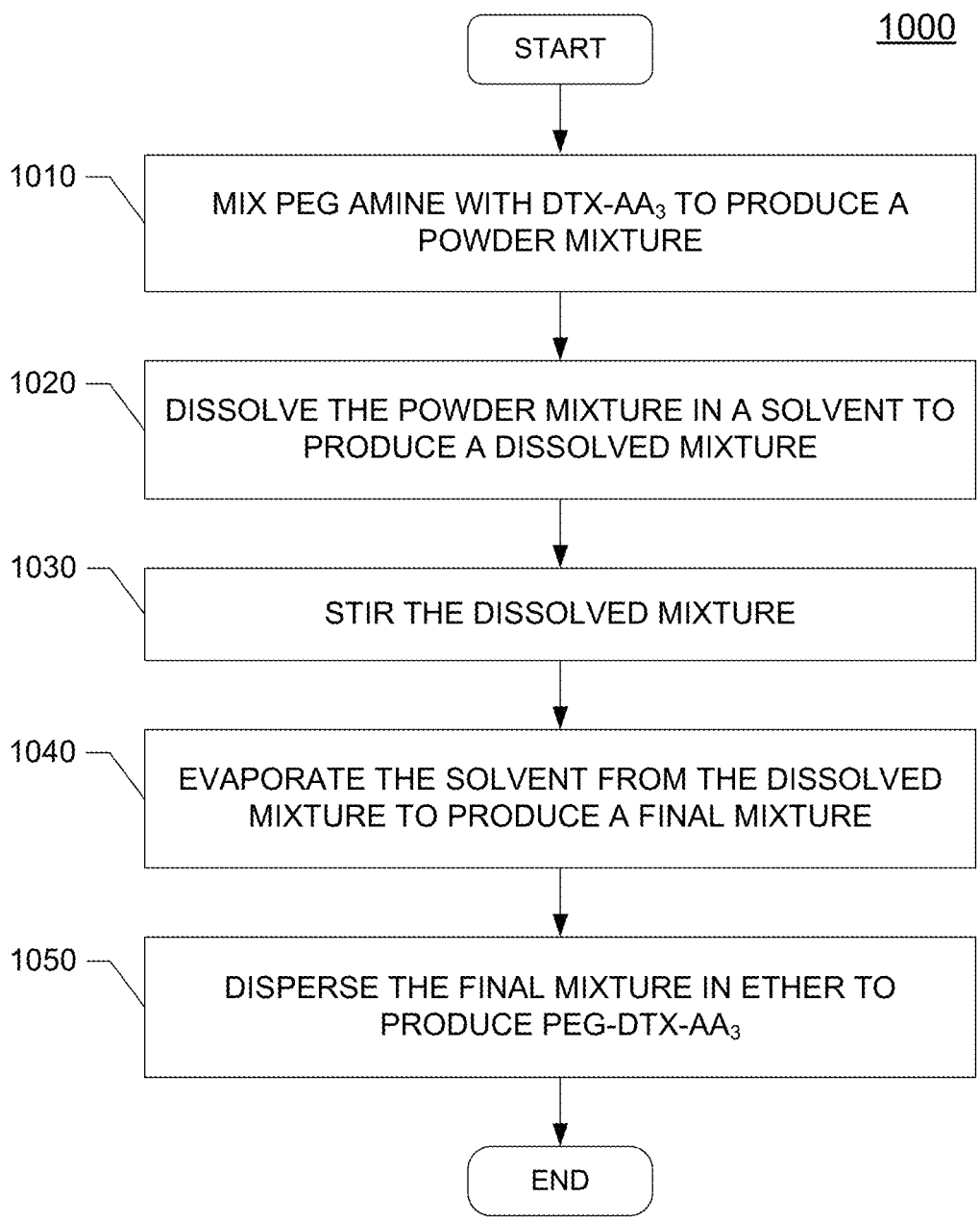
FIG. 10 is a method of synthesizing PEG-DTX-AA$_3$ 704 in accordance with one implementation of the present disclosure.

FIG. 10 is a method 1000 of synthesizing $PEG-DTX-AA_3$ 704 in accordance with one implementation of the present disclosure. In the illustrated implementation of FIG. 10, PEG amine is mixed with $DTX-AA_3$, at block 1010, to produce a powder mixture. The powder mixture is dissolved in a solvent, at block 1020, to produce a dissolved mixture, which is stirred, at block 1030. The solvent is then evaporated from the dissolved mixture, at block 1040, to produce a final mixture, which is then dispersed in ether, at block 1050, to produce $PEG-DTX-AA_3$.

In one implementation, the method 1000 further includes centrifuging and decanting the ether to remove the impurities from the final mixture. In one implementation, mixing includes mixing in a flask. In one implementation, the solvent includes tetrahydrofuran. In one implementation, the dissolved mixture is stirred for approximately 8 to 12 hours. In one implementation, evaporating the solvent comprises evaporating the solvent using a rotary evaporator at room temperature.

There are several benefits of the results produced by the above-described methods and formulations over the results produced by the conventional methods. The benefits include: (a) Convenience of synthesis and purification, wherein the drug-OAH conjugate synthesis is possible without using a coupling reagent; (b) Reduction of the side effects through the synthesis of the drug-OAH conjugate, wherein toxicity can be alleviated while maintaining the medicinal effect of small molecule drugs; (c) The pharmaceutical composition (drug-AOH) may be used alone or as a combination therapeutic agent using a combination of two or more, and the composition may be applicable to abnormal cell proliferation and diseases caused by infection, such as cancer and viral infection; and (d) Flexibility in the formulation of the drugs for different administration, wherein the pharmaceutical composition and the polymer compound can be developed for intravascular, subcutaneous injection, and/or oral administration (e.g., enteric and sustained-release preparation).

The description herein of the disclosed implementations is provided to enable any person skilled in the art to make or use the present disclosure. Numerous modifications to these implementations would be readily apparent to those skilled in the art, and the principals defined herein can be applied to other implementations without departing from the spirit or scope of the present disclosure. Thus, the present disclosure is not intended to be limited to the implementations shown herein but is to be accorded the widest scope consistent with the principal and novel features disclosed herein.

Those of skill in the art will appreciate that the various illustrative modules and method steps described herein can be implemented as electronic hardware, software, firmware or combinations of the foregoing. To clearly illustrate this interchangeability of hardware and software, various illustrative modules and method steps have been described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the present disclosure. In addition, the grouping of functions within a module or step is for ease of description. Specific functions can be moved from one module or step to another without departing from the present disclosure.

All features of each above-discussed example are not necessarily required in a particular implementation of the present disclosure. Further, it is to be understood that the description and drawings presented herein are representative of the subject matter which is broadly contemplated by the present disclosure. It is further understood that the scope of the present disclosure fully encompasses other implementations that may become obvious to those skilled in the art and that the scope of the present disclosure is accordingly limited by nothing other than the appended claims.

The invention claimed is:

1. A method for synthesizing a drug-organic-acid-anhydride conjugate using docetaxel as a drug, the method comprising:

mixing aconitic anhydride with a chlorinating reagent to produce a first liquid mixture by adding drop-wise the chlorinating reagent to the aconitic anhydride, wherein the chlorinating reagent comprises an reagent selected from the group consisting of phosphorus pentachloride ($PCl_3$), thionyl chloride, and oxalyl chloride;

dissolving the first liquid mixture in an organic solvent to produce a dissolved mixture, wherein the organic solvent comprises a solvent selected from the group consisting of methylene chloride, chloroform, and tetrahydrofuran (THF);

stirring the dissolved mixture;

evaporating the organic solvent from the dissolved mixture to produce a second mixture;

washing the second mixture with an impurity remover to remove impurities and to produce aconitic anhydride chloride, wherein the impurity remover is cyclohexane, wherein washing the second mixture with the impurity remover comprises dispersing the second mixture in the cyclohexane and centrifuging and decanting the cyclohexane to remove the impurities to produce the aconitic anhydride chloride; and mixing the docetaxel with the aconitic anhydride chloride to produce the drug-organic- acid-anhydride conjugate, wherein the drug-organic-acid-anhydride conjugate is a docetaxel- aconitic anhydride conjugate of Formula DTX-AA3:

Formula DTX-AA3.

2. The method of claim 1, wherein the chlorinating reagent is phosphorus pentachloride.

3. The method of claim 1, wherein stirring the dissolved mixture comprises stirring the dissolved mixture for approximately 1 to 2 hours.

4. The method of claim 1, wherein the organic solvent is methylene chloride.

5. The method of claim 1, wherein evaporating the organic solvent comprises evaporating the organic solvent using a rotary evaporator at room temperature.

6. The method of claim 1, wherein the impurities are removed based on solubility of the impurities in the impurity remover.

7. The method of claim 1, wherein the aconitic anhydride chloride is in liquid form.

* * * * *